(12) United States Patent
Mayer et al.

(10) Patent No.: US 9,888,920 B2
(45) Date of Patent: Feb. 13, 2018

(54) CONNECTING A PLURALITY OF TISSUE PARTS

(75) Inventors: Jorg Mayer, Niederlenz (CH); Mario Lehmann, Les Pommerats (CH); Andrea Mueller, Winterthur (CH); Andreas Wenger, Muri b. Bern (CH)

(73) Assignees: SPORTWELDING GMBH, Schlieren (CH); WOODWELDING AG, Stansstad (CH)

(*) Notice: Subject to any disclaimer, the term of this patent is extended or adjusted under 35 U.S.C. 154(b) by 804 days.

(21) Appl. No.: 13/823,174

(22) PCT Filed: Sep. 19, 2011

(86) PCT No.: PCT/CH2011/000220
§ 371 (c)(1),
(2), (4) Date: May 2, 2013

(87) PCT Pub. No.: WO2012/037697
PCT Pub. Date: Mar. 29, 2012

(65) Prior Publication Data
US 2013/0214026 A1 Aug. 22, 2013

Related U.S. Application Data

(60) Provisional application No. 61/384,919, filed on Sep. 21, 2010.

(51) Int. Cl.
*A61B 17/08* (2006.01)
*A61B 17/068* (2006.01)
(Continued)

(52) U.S. Cl.
CPC ........ *A61B 17/068* (2013.01); *A61B 17/0401* (2013.01); *A61B 17/064* (2013.01);
(Continued)

(58) Field of Classification Search
CPC . A61B 17/0401; A61B 17/068; A61B 17/064; A61B 17/0686; A61B 17/320068;
(Continued)

(56) References Cited

U.S. PATENT DOCUMENTS 3,657,056 A 4/1972 Winston
4,761,871 A * 8/1988 O'Connor ............. B29C 65/562
156/92

(Continued)

FOREIGN PATENT DOCUMENTS

EP 1728474 12/2006
JP 6-47048 2/1994
(Continued)

*Primary Examiner* — Eric Rosen
*Assistant Examiner* — Son Dang
(74) *Attorney, Agent, or Firm* — Rankin, Hill & Clark LLP

(57) ABSTRACT

A device for fixing a first and a second tissue part or a tissue part and an implant part to each other is provided, providing a fastener including a thermoplastic material and a fastening instrument. The fastening instrument includes a first instrument component with a first contact surface facing toward a distal side and a second instrument component has a foot with a second contact surface distally of the first contact surface and facing toward a proximal side. The first instrument component and the second instrument component are displaceable with respect to each other, so that the fastener is compressible between the first and second contact surfaces by application of a relative force between the components. The instrument also includes an energy source for coupling mechanical energy into one of the instrument components to soften and/or melt an end portion of the fastener.

8 Claims, 6 Drawing Sheets

(51) Int. Cl.
*A61B 17/04* (2006.01)
*A61B 17/064* (2006.01)
*A61B 17/32* (2006.01)
*A61B 17/00* (2006.01)

(52) U.S. Cl.
CPC .. *A61B 17/0686* (2013.01); *A61B 17/320068* (2013.01); *A61B 2017/00955* (2013.01); *A61B 2017/0408* (2013.01); *A61B 2017/0409* (2013.01); *A61B 2017/0417* (2013.01); *A61B 2017/0419* (2013.01); *A61B 2017/0464* (2013.01); *A61B 2017/0641* (2013.01); *A61B 2017/0647* (2013.01); *A61F 2220/0008* (2013.01)

(58) Field of Classification Search
CPC .... A61B 2017/0417; A61B 2017/0464; A61B 2017/0647; A61B 2017/00955; A61B 2017/0409; A61B 2017/0419; A61B 2017/0641; A61B 2017/0408; A61F 2220/0008
See application file for complete search history.

(56) References Cited

U.S. PATENT DOCUMENTS

| | | | |
|---|---|---|---|
| 5,163,960 A * | 11/1992 | Bonutti | A61B 17/0401 128/898 |
| 5,649,937 A | 7/1997 | Bito | |
| 6,585,750 B2 | 7/2003 | Bonutti et al. | |
| 7,867,252 B2 * | 1/2011 | Criscuolo | A61B 17/068 411/16 |
| 7,996,975 B1 * | 8/2011 | Denslow | F16B 5/04 29/419.1 |
| 8,357,201 B2 * | 1/2013 | Mayer | A61F 2/30 623/18.11 |
| 9,556,891 B2 * | 1/2017 | Toyozumi | B29C 65/08 |
| 2002/0068947 A1 * | 6/2002 | Kuhns | A61B 17/064 606/143 |
| 2004/0030341 A1 * | 2/2004 | Aeschlimann | A61B 17/00491 606/232 |
| 2007/0038220 A1 * | 2/2007 | Shipp | A61B 17/064 606/326 |
| 2007/0250118 A1 | 10/2007 | Masini | |
| 2007/0270833 A1 * | 11/2007 | Bonutti | A61B 17/0401 606/28 |
| 2008/0287989 A1 * | 11/2008 | Weisel | A61B 17/0401 606/220 |
| 2009/0216253 A1 * | 8/2009 | Bell | A61B 46/30 606/153 |
| 2009/0317768 A1 * | 12/2009 | Mayer | A61B 17/68 433/201.1 |
| 2010/0049179 A1 | 2/2010 | Kanaoka et al. | |
| 2010/0179654 A1 | 7/2010 | Mayer et al. | |
| 2012/0016413 A1 | 1/2012 | Timm et al. | |
| 2012/0029538 A1 * | 2/2012 | Reeser | A61B 17/064 606/151 |
| 2012/0150080 A1 | 6/2012 | Hathaway et al. | |
| 2013/0109925 A1 | 5/2013 | Horton et al. | |
| 2014/0276969 A1 * | 9/2014 | Wenchell | A61B 17/10 606/139 |

FOREIGN PATENT DOCUMENTS

| | | |
|---|---|---|
| WO | 99/09891 | 3/1999 |
| WO | 02/069817 | 9/2002 |

* cited by examiner

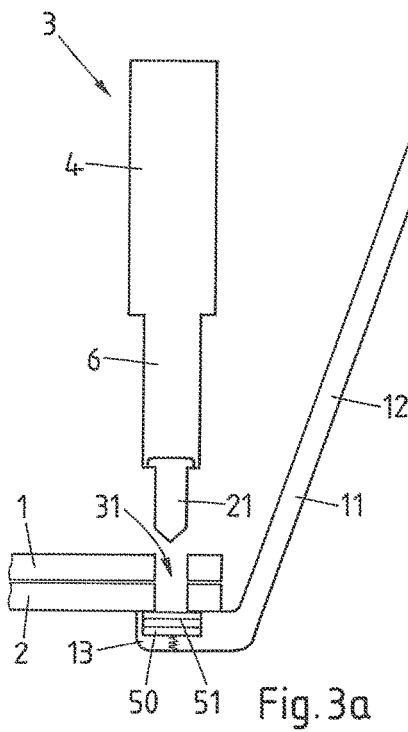
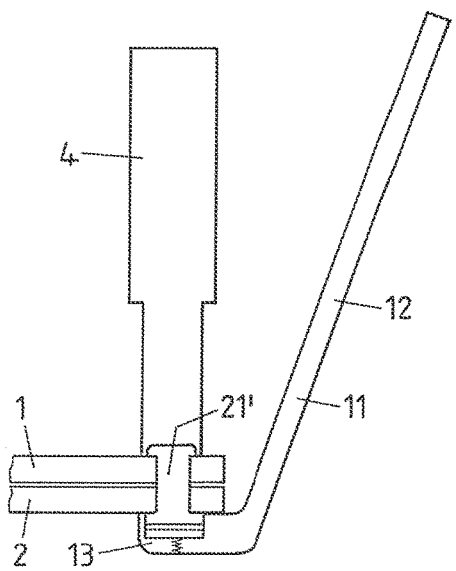
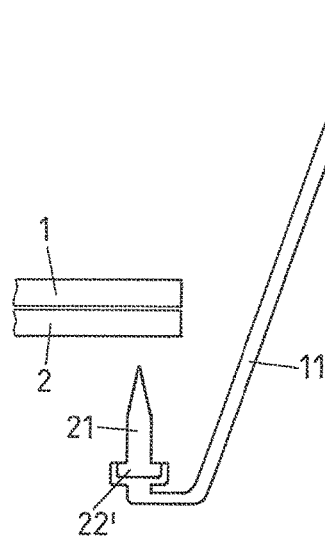
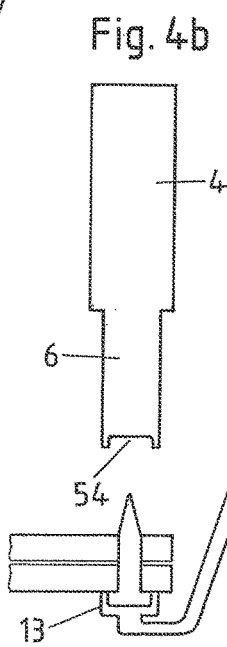
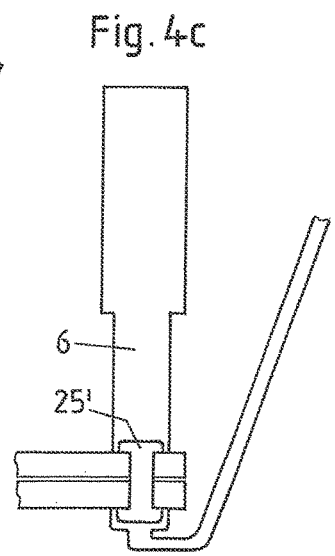

CONNECTING A PLURALITY OF TISSUE PARTS

BACKGROUND OF THE INVENTION

Field of the Invention

The invention is in the field of medical technology and relates to methods and devices of fixing two or more tissue parts to each other or for affixing at least one tissue part to an implanted device.

Description of Related Art

In surgery, it is often necessary to affix two tissue parts to each other or to affix an implanted device—such as a so-called mesh—to a tissue part. While a lot of methods for affixing two bone parts to each other have become known, these rely on the anchoring capacity of the hard tissue in which fasteners may be anchored safely of being removed by pulling forces. It is, however, often a challenge to affix two tissue parts to each other which are not bone tissue but for example cartilage or soft tissue. The same challenge exists if an implanted device is to be affixed to cartilage or soft tissue.

BRIEF SUMMARY OF THE INVENTION

It is an object of the present invention to provide methods and devices for fixing tissue parts (portions or organs of human or animal tissue) to each other or of fixing an implant part to a tissue part, the methods and devices overcoming drawbacks of prior art methods and devices and/or being especially suitable for tissue parts that are not bone tissue and/or not dimensionally stiff.

In accordance with an aspect of the invention, a method of fixing a first and a second tissue part or a tissue part and an implant part to each other is provided. The method comprises the steps of providing a fastener comprising a thermoplastic material (generally at least at an end portion), providing a fastening instrument, the fastening instrument comprising a first instrument component with a first contact surface and a second instrument component with a second contact surface, the first instrument component and the second instrument component being displaceable with respect to each other, positioning the fastener and the fastening instrument so that the fastener reaches through a common opening of the first and second tissue or implant parts, which common opening is constituted by a first through opening of the first tissue or implant part and a second through opening of the second tissue or implant part, the first and second through openings aligned with each other, and so that the first contact surface is in contact with a proximal end face of the fastener and the second contact surface is in contact with a distal end face of the fastener. The method also comprises the steps of submitting the first and second instrument components to a relative force so that the fastener is pressed between the first and second contact surfaces, and simultaneously coupling mechanical vibrations into at least one of the first and second instrument components with a vibration power and during a vibration time sufficient to at least partially soften and/or melt an end portion under the common impact of the relative force and the vibrations, and using the softening and/or melting of the end portion to provide the end portion with a head with a diameter greater than a diameter of at least one of the through openings, and letting the softened and/or melted distal end portion re-solidify.

The invention also pertains to thermoplastic material (for example any one of the hereinafter explicitly mentioned materials) for use as a fastener or fastener part(portion) in such a methods. Especially, such use pertains to a fastener part that can be deformed and/or melted to be provided with a distal or proximal head, either by deformation of the thermoplastic material or by the thermoplastic material being welded to an also thermoplastic head shaping element as explained hereinafter. All remarks and teachings in this text that relate to the method also pertain to the thermoplastic material for use as a fastener or fastener part in such a method.

Returning to the method, the steps of positioning the fastener and of positioning the instrument may be done, depending on the set-up and possibly on the wishes of the surgeon, in any sequence or simultaneously or partially simultaneously.

In the step of using the softening and/or melting of the end portion to provide the end portion with a head, the end portion may be caused to deform, under the common impact of the relative force and the vibrations, to yield the head.

This may for example be done such that the end portion itself is deformed into the head, i.e. the head material may be deformed end portion material.

In an alternative embodiment, the instrument component at the contact surface of which the head portion is formed may comprise a head forming element that under the impact of the vibrations and the relative force is welded to the fastener's end portion so that the fastener after the step of letting the end portion re-solidify comprises the initial fastener material plus the head forming element material. To this end, the named instrument component (for example the second instrument component, which is in contact with the distal end of the fastener and which has a foot) may comprise a head forming element dispenser.

The through openings in the tissue parts or the tissue part and the implant part may be naturally present (or pre-manufactured in case of an implant part), may be pre-made in a preparation step (for example by drilling) prior to the insertion of the fastener, or may be made by the insertion of the fastener that then for example comprises a piercing tip or edge (or generally a reaming capacity). Combinations are possible, for example a pre-made through opening in one part combined with an opening made by the insertion in the other part, or any other combination. Also it is possible that the opening is partly pre-made; for example a pre-made or naturally present opening with a first, smaller cross-sectional area exists and is additionally widened by the insertion of the fastener to a second, larger cross sectional area by the insertion of the fastener.

In embodiments, the fastener is generally inserted from a proximal side, which side is also the side that can be accessed by the surgeon during operation. Then, the end portion that is deformed to yield a head is the distal end portion.

In alternative embodiments, the fastener is inserted from a distal side. To this end, the fastener may be, prior to the placing of the instrument (or at least of the second instrument component of the instruments are separate) at the operation site, provisionally attached to the second instrument component. As a possibility, the second instrument component may comprise a dispenser that is, during the process, in contact with the distal end of the fastener and sequentially dispenses a plurality of fasteners.

As soon as the softening and/or melting sets in, the relative force will cause a relative movement of the first and second instrument components, whereby the first and second contact surfaces are moved towards each other and the fastener is thus compressed.

In an aspect of the invention, it is therefore proposed to use mechanical vibrations, such as ultrasonic vibrations, to deform an end portion, (that may be a distal portion or a proximal portion) of a fastener into a (distal or proximal, respectively) head. As a consequence, the fastener functions as a kind of rivet. In this, the fastener initially may be a fastening pin of arbitrary cross section. Also, the fastener may optionally comprise a pre-formed head on the other (proximal or distal, respectively) side In many embodiments, the second instrument component has a proximal shaft portion and a distal foot portion, wherein the second contact surface is formed as a proximally facing surface of the foot portion or a part thereof. In embodiments, the second contact surface may be approximately perpendicular to a proximodistal fastener axis.

In many embodiments, the first instrument component—that impinges on the fastener from the proximal side thereof—is used to cause the mechanical vibrations to impinge on the fastener, for example by coupling the mechanical vibrations into the fastener. To this end, the instrument may further comprise a mechanical vibration generator, such as a vibration generator that comprises a piezoelectric element and an electric excitation circuitry for the piezoelectric element. The first instrument component may act as a sonotrode of the instrument, which sonotrode is coupled to the vibration generator. The instrument may further comprise an instrument housing, in which the vibration generator with the sonotrode coupled thereto is housed. The housing may but need not completely seal off the vibration generator. The second instrument component then may be a counter element that is for example movably mounted relative to the first instrument component (and to the housing if present) or that can be held by the surgeon like a separate tool. The second instrument component may comprise a distal counter portion (that may be the foot portion) with the second contact surface facing towards the proximal side and a shaft portion extending proximally from the counter portion. The shaft portion may be slidingly (or pivotingly) mounted to the housing and the relative force may be applied at the shaft portion.

As an option, in embodiments of the invention, the second instrument component may be configured to deflect the mechanical oscillations generated by the vibration generator. This may for example be done by an instrument component that has a vibrating element into which transversal oscillations along an input axis are deflected into transversal oscillations along an output axis. An example of such a device is taught in WO 2007/101 362. Embodiments that comprise the deflection of mechanical oscillations are especially suited in situations where a straight access along the axis of the fastener is difficult and where the operation site is better accessed from sideways. It is one of the advantages of embodiments of the invention that they are also suited for insertion by an access from sideways.

Also as an option, a plurality of fasteners can be used. For example, the plurality of fasteners can be distributed over the tissue/implant parts. The heads of neighbouring fasteners can then optionally be configured to be in contact with each other or be welded to each other.

In accordance with an option, the tissue parts fixed to each other are at the same time provided with one or more flexible planar structure(s) of an artificial material for reinforcement. As an example, such flexible planar structure may be a mesh. Such flexible planar structure may be provided on an outer side of the tissue portions, on outer sides of tissue portions and/or between the tissue portions. Alternatively, if an implant part is fixed to a tissue part, such a flexible planar structure may constitute the implant part.

The first and second tissue parts may be parts of a common tissue element or organ. For example, the first and second tissue parts may be portions of a ruptured or partially ruptured tissue element or organ of which a rupture has to be healed. The first and second tissue parts as an alternative may be separate elements and/or organs, for example a flat, bendable implant to be affixed to a flat, bendable tissue part.

The first and second tissue parts may for example by layers or other parts of cartilage. An application of aspects of the method of the invention is a repair of the meniscus. In the preparation for the method, end portions of a ruptured meniscus are bent to be laid on top of each other, and the first and second openings are made into the assembly of the portions on top of each other.

As an alternative to cartilage, at least one of the first and second tissue parts may be parts of other tissue, especially soft tissue, or a tissue replacement material. One of the first and second tissue parts may also be an implant to be affixed to a tissue part. In this text, for reasons of simplicity the parts to be affixed to each other are often referred to as "first and second tissue parts", however, embodiments of the invention also pertain to in-situ affixing an artificial element (implant) to a tissue part.

The invention also applies to fixing more than two tissue parts, for example three or more tissue parts to each other in one step, by laying the three (or more) tissue parts on top of each other and introducing the fastener in a common, aligned hole.

While many embodiments of methods and devices according to the invention are especially suited for affixing cartilage or soft tissue parts to each other or of affixing artificial devices (implant parts) to such tissue, the application to dimensionally stiff bone tissue is not excluded in all embodiments. Rather, the methods and devices may also be suitable for bone tissue, especially for flat bone (ossa plana) or weak bone tissue.

It is a further option to use the method and device to fasten a filament-like element, such as a thread surgical (especially a thread for a surgical suture), to tissue. As an example, such a filament-like element may be attached to the tissue parts or the tissue part and the implant part fixed to each other during the fixation process. For example a loop of the filament-like element may be wound around a shaft of the fastener and held by a head of the fastener (a pre-fabricated head or the head that is provided using the softening and/or melting of the end portion). As another example, such a filament-like element constitutes the implant part, the loop then forming the through opening aligned with a through opening in the tissue part.

More in general, the invention according to an aspect concerns a method of anchoring a filament-like element, especially a thread, in a tissue part. The method comprises the steps of providing a fastener, the fastener comprising a first head at a first fastener end portion; providing a fastening instrument, the fastening instrument comprising a first instrument component with a first contact surface and a second instrument component with a second contact surface, the first instrument component and the second instrument component being displaceable with respect to each other; and positioning the fastener and the fastening instrument so that the fastener reaches through an opening of the tissue, and so that the first contact surface is in contact with a proximal end face of the fastener and the second contact surface is in contact with a distal end face of the fastener. The method also comprises the steps of coupling, by at least one of the instrument components, energy into the fastener to cause a second fastener end portion to at least partly soften and/or melt, and to use the softening and/or melting of the second end portion to provide the second end portion with a second head with a diameter greater than a diameter the opening; and letting the softened and/or melted end portion re-solidify, wherein filament-like element forms a loop around the fastener, a diameter of the loop being smaller than at least one of the first head and the second head.

In accordance with an embodiment, the filament-like element is positioned by a positioning element (such as a needle or other element, possibly the fastener itself) to which it is mounted. This element in accordance with an embodiment is inserted through the tissue part from a distal side in a manner that an end portion of the filament-like element, which end portion forms the loop, is accessible from the proximal side.

If the positioning element is a needle, it may be a needle of a shape memory material and be guided in a channel of the second instrument component to be pushed from the proximal side, to pierce the tissue from the distal side and to take along the thread (or other filament-like element) through the tissue back to the proximal side.

In many embodiments, the second instrument component (or the first instrument component if the fastener is introduced from the distal side) has a head shaping portion that forms the second (or first, respectively) contact surface. The head shaping portion may be provided as a for example shallow indentation—if present in the counter portion/foot portion—a bottom of which forms the second (first) contact surface. The head shaping portion may further comprise at least one energy director or a partitioning structure ensuring a desired material flow to different directions. The head shaping portion may for example have a concave or partially concave shape. By the method according to an aspect of the invention, the distal head that is shaped comprises surface portions that are a replica of the head shaping portion.

In any aspect of the method, one or an arbitrary (meaningful) combination of the following may occur. Mechanical oscillations may be coupled into the fastener from the first instrument component during the step of positioning the fastener. The fastener may be generally pin-shaped with a cylindrical portion (of any suitable cross section, i.e. circular or non-circular), possibly with a pre-formed (proximal, or distal) head portion. As an alternative to being pin-shaped, the fastener may comprise a plurality of shafts that are connected by a proximal (or distal) bridge portion, the shafts being configured to be reach through a corresponding number of common openings of the first and second tissue or implant parts. The fastener may comprise a pre-made proximal (or distal) head portion that forms a shoulder that abuts against the first tissue part when the force and the vibrations are coupled into the fastener. The fastener may consist of thermoplastic material, or the fastener may comprise a thermoplastic component (that comprises at least the—distal or proximal—end portion) and a component that is not thermoplastic.

During the simultaneous steps of coupling vibrations into the fastener and compressing the fastener between the first and second instrument components, a thermoplastic portion at the other end (the proximal end of the fastener is inserted from the proximal side or the distal end if the fastener is inserted from the distal side) of the (for example pin-shaped) fastener may be deformed into a proximal/distal further head. If the fastener comprises a pre-shaped further (proximal/distal) head that is made of a thermoplastic material, the pre-shaped further head portion may optionally be shaped further, so that for example its distal/proximal shoulder has a shape adapted to the shape of the first tissue part.

The fastener may comprise a proximal guiding and/or retaining structure into which a corresponding guiding and/or retaining element of the first instrument component may engage so as to guide and/or hold the fastener during insertion thereof.

In addition to the vibration generator, the instrument may further comprise a force applicator for automatedly applying the relative force. Such a force applicator may for example comprise a spring that may be pre-tensioned prior to the process, and the spring force may be released simultaneously with generating the vibrations. Alternatively, a force applicator may comprise another driving mechanism such as an electrically actuated mechanism.

In addition to a force applicator or as an alternative thereto, the instrument may comprise a handle to allow the surgeon to apply the force himself. Then, the instrument may optionally further comprise a resistance spring against the force of which the relative force has to be applied and the first and second instrument components have to be moved relative to one another. Such a spring may ease the releasing of the instrument components from the fastener after solidification of the thermoplastic material.

Thermoplastic material of the fastener may be caused to adhere to the tissue of the first and/or the second tissue part and/or be caused to interpenetrate structures of the first and/or second tissue part to create a positive-fit connection. This may be thermoplastic material of the proximal and/or distal head portion and/or of a remaining cylindrical portion between the head portions.

A fastening instrument for fixing a first and a second tissue part or a tissue part and an implant part to each other or for anchoring a filament-like element, for example a thread, in a tissue. The fastening instrument comprises a first instrument component with a first contact surface and a second instrument component with a second contact surface, the first instrument component and the second instrument component being displaceable with respect to each other, wherein the first instrument component has a first contact surface facing towards a distal side. The second instrument component has a foot with a second contact face distally of the first contact face and facing towards a proximal side, so that a fastener is compressible between the first and second contact faces by application of a relative force between the first and second instrument components. The instrument further comprising an energy source for coupling mechanical energy into at least one of the first and second instrument components.

The contact face, in contact with which the end portion is provided with a head, may comprise a head shaping portion. For example for a fastener inserted from a proximal side, the second contact face of the foot of the second instrument component then is formed as a head shaping portion. If the fastener is inserted from the distal side, the distal end face of the first instrument component may comprise a head shaping portion. In addition, the in each case other contact face may optionally also comprise a head shaping portion.

At least the first and second instrument components are capable of being sterilized.

A kit of parts a for fixing a first and a second tissue part or a tissue part and an implant part to each other comprises an instrument of the above-described kind and further comprises at least one fastener, the fastener comprising a proximal and a distal end, wherein the proximal and/or the distal end comprises thermoplastic material that can be made deformable/flowable by the impact of the mechanical energy. The fastener may be generally pin-shaped with an optional proximal head and with an optional distal cutting and/or punching and/or reaming structure.

For example, the at least one fastener is provided in a sterile package.

As an alternative to mechanical vibrations, other forms of mechanical energy may be used to make the thermoplastic material flowable/deformable. This especially includes rotational movement of the fastener relative to the counter element. As yet another alternative, electromagnetic radiation may be used to make the thermoplastic material flowable/deformable. To this end, the fastener may be essentially transparent with a radiation absorber especially in the distal region. The radiation may be coupled into the fastener by means of a laser or other radiation source.

In this text the expression "thermoplastic material being capable of softening and/or being melted by the impact of mechanical vibration" or in short "liquefiable thermoplastic material" or "liquefiable material" is used for describing a material comprising at least one thermoplastic component, which material becomes liquid or flowable when heated, in particular when heated through friction i.e. when arranged at one of a pair of surfaces (contact faces) being in contact with each other and vibrationally or rotationally moved relative to each other, wherein the frequency of the vibration is between 2 kHz and 200 kHz, preferably 20 to 40 kHz and the amplitude between 1 µm and 100 µm, preferably around 10 to 30 µm. Such vibrations are e.g. produced by ultrasonic devices as e.g. known for dental applications. For being able to be load-bearing connection, the material may have elasticity coefficient of more than 0.5 GPa, preferably more than 1 GPa. The elasticity coefficient of at least 0.5 GPa also ensures that the liquefiable material is capable of transmitting the ultrasonic oscillation with such little damping that inner liquefaction and thus destabilization of the liquefiable element does not occur, i.e. liquefaction occurs only where the liquefiable material is at the liquefaction interface to the stop face. The plastification temperature is preferably of up to 200° C., between 200° C. and 300° C. or even more than 300° C. Depending on the application, the liquefiable thermoplastic material may or may not be resorbable.

Suitable resorbable polymers are e.g. based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplastics such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LOPS), polyacetals, halogenated polymers, in particular halogenated polyoelefins, polyphenylene sulphides, polysulphones, polyethers, polypropylene (PP), or corresponding copolymers or blended polymers or composite materials containing the mentioned polymers as components are suitable as non-resorbable polymers. Examples of suited thermoplastic material include any one of the polylactide products LR708 (amorphous Poly-L-DL lactide 70/30), L209 or L210S by Böhringer Ingelheim.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate by DSM). An overview table of polymers and applications is listed in Wintermantel, page 150; specific examples can be found in Wintermantel page 161 ff. (PE, Hostalen Gur 812, Höchst AG), pages 164 ff. (PET) 169ff. (PA, namely PA 6 and PA 66), 171 (PTFE), 173 ff. (PMMA), 180 (PUR, see table), 186 ff. (PEEK), 189 ff. (PSU), 191 (POM—Polyacetal, tradenames Delrin, Tenac, has also been used in endoprostheses by Protec).

The liquefiable material having thermoplastic properties may contain foreign phases or compounds serving further functions. In particular, the thermoplastic material may be strengthened by admixed fillers, for example particulate fillers that may have a therapeutic or other desired effect. The thermoplastic material may also contain components which expand or dissolve (create pores) in situ (e.g. polyesters, polysaccharides, hydrogels, sodium phosphates) or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed.

If the liquefiable material is to be liquefied not with the aid of vibrational energy but with the aid of electromagnetic radiation, it may locally contain compounds (particulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity; or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see S M Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 µm (contents, preferentially 10-25% by volume), sub-micron (nanofillers as from precipitation, preferentially plate like aspect ratio>10, 10-50 nm, contents 0.5 to 5% by volume).

BRIEF DESCRIPTION OF THE DRAWINGS

Hereinafter, embodiments of the invention are described referring to drawings. In the drawings which are schematics and not to scale, same reference numerals refer to same or corresponding elements. The figures show:

FIGS. 3a and 3b are elevation views showing an alternative fastener-instrument-arrangement prior in two different process steps of a process of affixing two tissue parts to each other;

FIG. 4a-4c are elevation views showing yet another embodiment of a fastener-instrument arrangement during different process steps of affixing two tissue parts to each other;

DETAILED DESCRIPTION OF THE INVENTION

Figure 1:
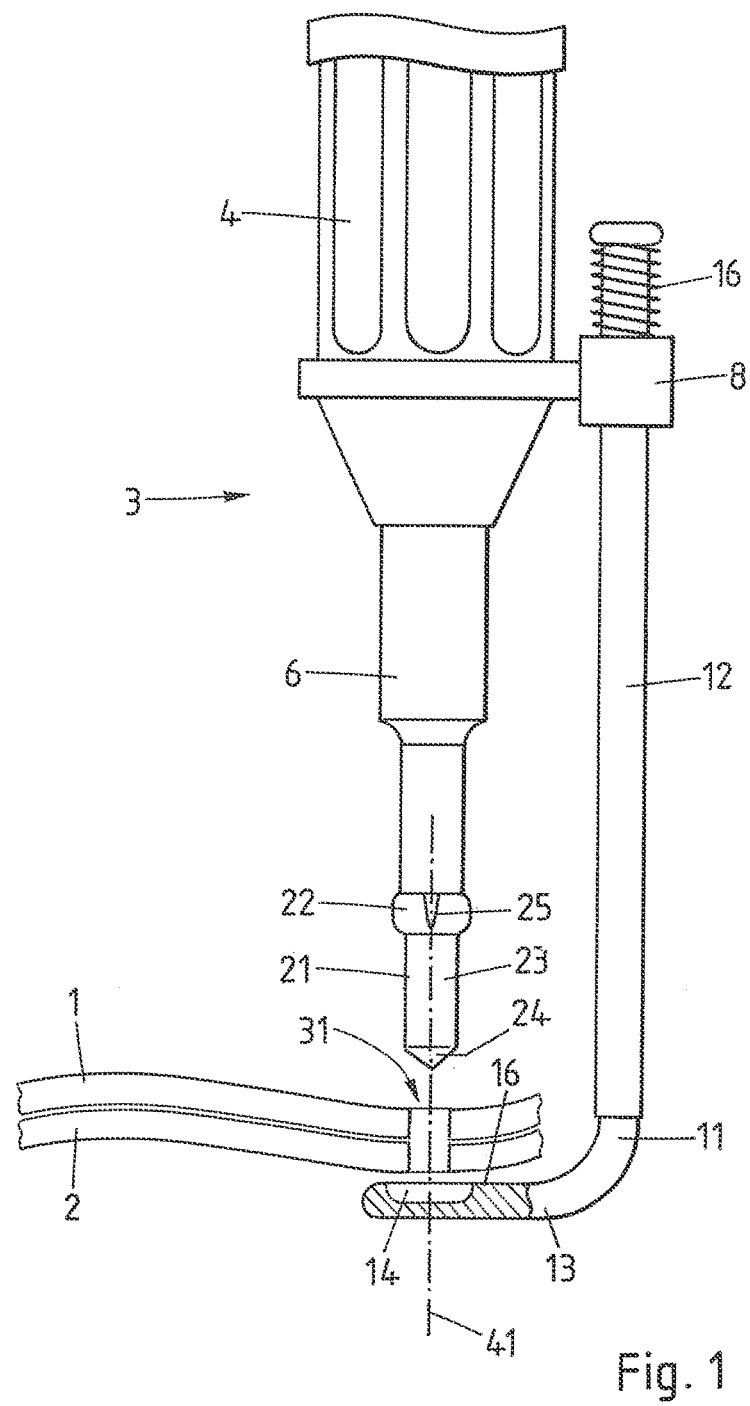
FIG. 1 is an elevation view of an instrument with a fastener positioned to affix two tissue parts to each other.

The first tissue part 1 and the second tissue part 2 shown in FIG. 1 may for example be parts of a ruptured meniscus. Edge portions of the meniscus along the rupture are positioned on top of each other. Alternatively, the first tissue part and the second tissue part may be other tissue portions to be affixed to each other; one of them may also be a tissue replacement and/or reinforcement implant. For example one or both of the tissue parts may be other cartilaginous tissue or a ligament or tendon or a intervertebral disc, or skin etc. A tissue replacement or reinforcement implant may for example be a mesh or allograft or artificial ligament or tendon or replacement of a cartilaginous tissue, etc. The method is not restricted to a particular kind of tissue/or implant but is especially suited for tissue that is different from bone or bone replacement material.

The instrument 3 comprises an instrument housing 4 in which an ultrasonic transducer (not shown) or other vibration generating device is arranged. The ultrasonic transducer or other vibration generating device is operable to set a sonotrode 6, being the first instrument component, into vibration. The second instrument component 11 is a counter element with a counter element shaft 12 and a foot 13. The shaft 12 is slidingly mounted to the housing 4 or (or to an other element coupled to the first instrument component). In the depicted configuration, this is done by a guiding element 8 affixed to the housing 4, the guiding element with a through hole having an inner diameter adapted to an outer diameter of the shaft portion and serving as guide an defining a relative, proximodistal movement direction.

The fastener 21 in the depicted configuration is pin-shaped with a cylindrical body or shaft 23 (that may be circular in cross section or have an other cross section adapted to the desired geometry) with an optional pre-formed proximal head 22 and consists of a thermoplastic material. A proximal guiding hole 25 is adapted to a holding protrusion of the sonotrode 6, so that the fastener 21 can be attached to the sonotrode. The fastener has a slightly tip-shaped distal en portion 24.

In the depicted configuration, a common opening 31 of the first and second tissue parts is pre-made; the diameter is, however, smaller than the diameter of the fastener. When the fastener is introduced into the opening, ultrasonic vibrations may be coupled into it so as to assist the widening process of the opening 31.

The foot 13 of the counter element 11 has an indentation 14 that is aligned to the sonotrode 6 and, if mounted, to the fastener. The fastener axis 41 may for example be an axis of the indentation 41. A diameter, or, more generally, an area of cross section, of the indentation is larger than a diameter/area of cross section of the cylindrical portion of the fastener. In the region of the indentation (if present) or generally at the spot where during compression of the fastener the fastener is in contact with the counter element, the counter element may comprise an optional coating of a non-sticking material so as to ease releasing the removal of the counter element from the fastener after the process.

In the depicted configuration, the instrument further comprises an optional spring 16. In accordance with a first option, the spring may in the configuration of FIG. 1 be pre-tensioned to pull the first and second instrument components towards each other so as to compress the fastener between the sonotrode 6 and the foot 13. This provides a pre-defined compression force during the compression step. In accordance with a second option, the spring may be such as to be compressed when the sonotrode and the counter element are pressed against each other so as to provide a release mechanism after the process.

Figure 2:
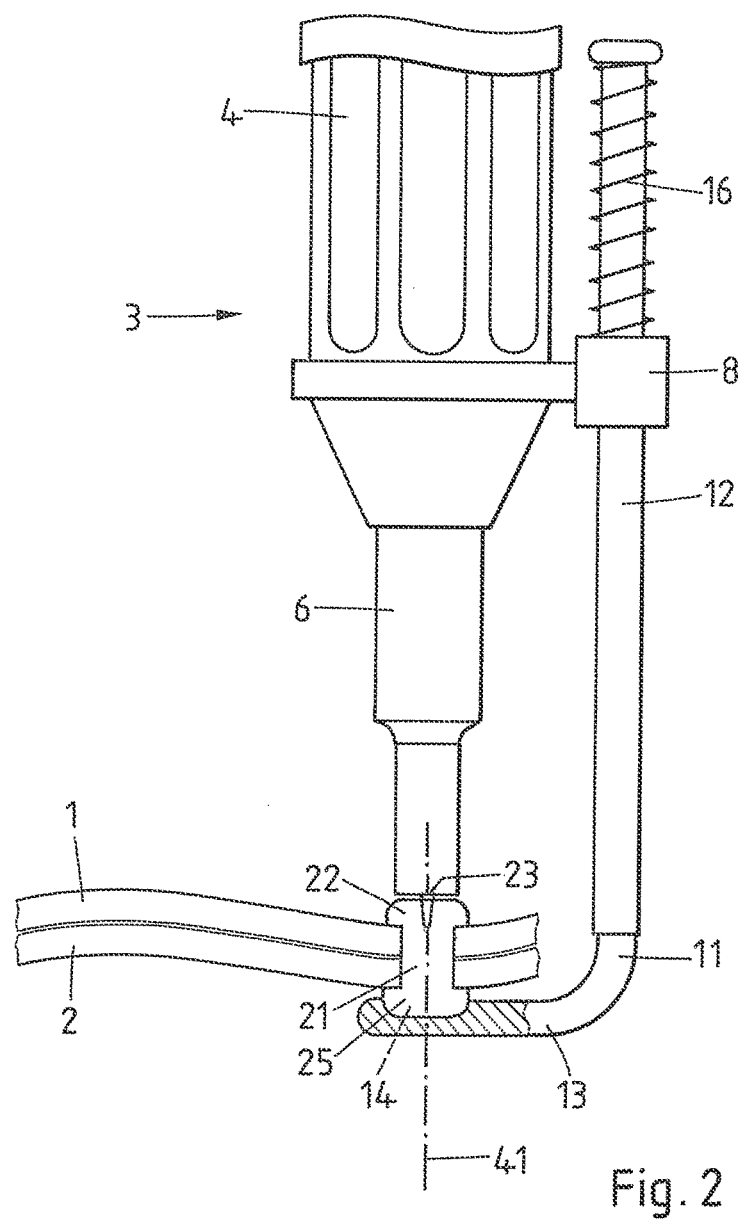
FIG. 2 is an elevation view showing the fastener and the instrument during the process of affixing the two tissue parts to each other.

FIG. 2 shows the assembly at the end of the step of simultaneously pressing the sonotrode and the counter element towards each other while coupling vibrations into the sonotrode and thus the fastener. The distal end of the fastener is deformed to yield a distal head 25 the shape of which is defined by the indentation. Also the proximal head 22 and/or the cylindrical portion may be deformed. The result of the process is a rivet that permanently clamps the two tissue parts on each other.

In the depicted configuration, the stiffness of the tissue parts is assumed to be sufficient so that the distal end of the fastener does not press the tissue against the bottom of the indentation. Rather, the second tissue parts lies against a flat portion 16 of the foot 13 proximal surface, which flat portion 16 surrounds the indentation 14. The fastener 21 pierces the tissue letting a space for the distal head to form underneath the second tissue part 2. In situations where the stiffness is not sufficient, the common opening may be pre-formed to have a diameter corresponding to the cylindrical portion of the fastener or slightly larger than the latter. In these embodiments, the tissue parts are advantageously provisionally fixed relative to each other after pre-forming the common opening, for example by surgical clamps. It is also possible to provide the fastener with a retractable punching sheath that first punches the common opening and is then retracted while the fastener body having the cylindrical portion remains in the opening; in these embodiments the fastener advantageously does not have a pre-formed proximal head, but the proximal head—like in other embodiments—is formed only during the process.

Also the sonotrode may comprise an indentation so as to define the shape of the proximal head.

A variant of the set-up shown in FIGS. 1 and 2 is depicted in FIGS. 3a and 3b. FIG. 3a shows the variant while the fastener 21 is introduced, and FIG. 3b shows it at the end of the step of causing material to be liquefied by the effect of mechanical energy.

As a first difference to the assembly in FIGS. 1 and 2, that the second instrument component 11 of the assembly on FIGS. 3a and 3b is not necessarily guided by a guiding element mechanically connected to the first instrument component but is held independently. For example, the surgeon performing the operation may hold the vibration generating instrument comprising the first instrument component in one hand and the second instrument component in the other hand.

Further, the second instrument component 11 comprises a magazine 50 of fastener head forming elements 51 that may be during the step of coupling mechanical vibrations into the fastener welded to the fastener so that the fastener after the step comprised the material of the head forming element in addition to the material it initially consisted of.

At least one distal head forming element carried by the second instrument component, for example in a magazine of head forming elements, may also be used in any embodiment. For example, it may be used together with a first instrument component of the kind shown in FIGS. 1 and 2, for example with the first instrument component comprising a guiding element for the second instrument component and/or a spring mechanism for automatically excerpting the necessary force. The head forming element magazine may comprise a spring or the like capable of automatically feeding a head forming element into the working position (where it forms part of the contact surface) when the last head forming element was used.

The embodiment of FIGS. 4a-4c shows a variant where the fastener 21 having a distal head 22' is initially carried by the second instrument component and is introduced from the distal side. To this end, the fastener may optionally be equipped to pierce the tissue parts (or tissue and implant portion) that it fastens together. A piercing fastener may also be used in embodiments where it is introduced from the proximal side.

In embodiments with a piercing fastener, the common opening need not be pre-made by a separate instrument or similar but may be made by introducing the fastener. As yet another alternative (that may be combined with any embodiment), an initial opening of at least one of the tissue parts may be smaller than the final common opening in at least one dimension and may be expanded by introducing the fastener.

FIG. 4a depicts the initial step of introducing the fastener from the distal side by the second instrument component 11. After this has been accomplished, the vibration generating instrument comprising the housing 4 and the second instrument component 6 (the sonotrode) is used to liquefy the proximal end portion of the fastener and to form a proximal head 25', as shown in FIGS. 4b and 4c. To this end, the sonotrode 6 comprises a distal head shaping portion being a shallow indentation 54 similar to the shallow indentation 14 of the foot in the previous embodiments.

While in the embodiments of FIGS. 1-3b the vibration energy is at least partially transmitted through the fastener and is primarily absorbed under the generation of heat at the distal end in contact with the foot, in the embodiment of FIGS. 4a-4c, absorption of vibration energy primarily takes place at the location of contact between the sonotrode and the fastener.

Figure 5A:
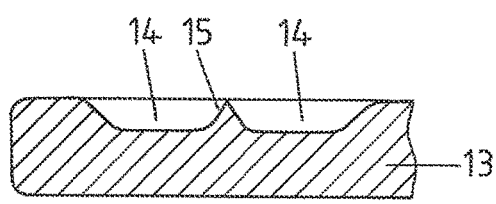
FIG. 5a is a sectional elevation view of a material guiding and energy directing structure.

Generally, at the site of liquefaction (at the distal end portion of the fastener in FIGS. 1-3b and at the proximal end portion in FIGS. 4a-4c), a head shaping portion may be provided in the second instrument component or the first instrument component, respectively. As described hereinbefore, the head shaping portion may comprise a surface structure that has the form of an indentation, for example a shallow indentation. The contour of the indentation then may correspond to the contour of the head that is to be formed. Further, the head shaping portion may comprise material directing and/or energy directing structures. Energy directing structures, as are known from the technology of ultrasonic welding, may help to determine the spot(s) at which liquefaction sets in when the vibration energy is coupled into the sonotrode. A material directing structure may help to distribute the molten material in a desired manner. FIG. 5a shows, in section, the end portion of a foot 13 of a second instrument component. In a middle of the indentation 14, a ridge 15 is formed that may serve both, as energy directing structure and as material directing structure for material from a fastener that is pressed against the foot (from above in the orientation shown in the figure) while mechanical vibrations are coupled into it. An analogous structure may be present in a sonotrode if a configuration as shown in FIGS. 4a-4c is chosen, where the fastener is introduced from the distal side.

Figure 5B:
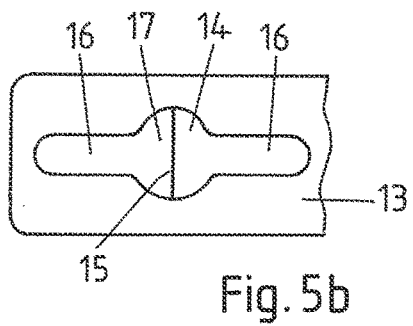
FIG. 5b is a plan view of a possible shape of a head shaping portion.

FIG. 5b yet shows a top view of an head shaping portion where the indentation 14 has an outer contour that is not circular but comprises a central section 17 the diameter of which may be similar to the diameter of the fastener or only slightly enhanced and lobes 16 extending in opposing directions. Almost arbitrary other shapes (circular, elliptical, one or more than two lobes, symmetrical or asymmetrical etc.) adapted to the requirements and geometrical conditions are possible; also the fastener's shaft need not be circular in cross section, because in contrast to prior art methods neither the insertion of the fastener nor any other step during the process necessarily requires a rotational movement of the fastener.

Whereas the head shaping portion in FIG. 5b is shown to be a structure of the foot 13, in embodiments that comprise insertion of the fastener from the distal side, such a structure may be present also at the sonotrode.

Figure 6:
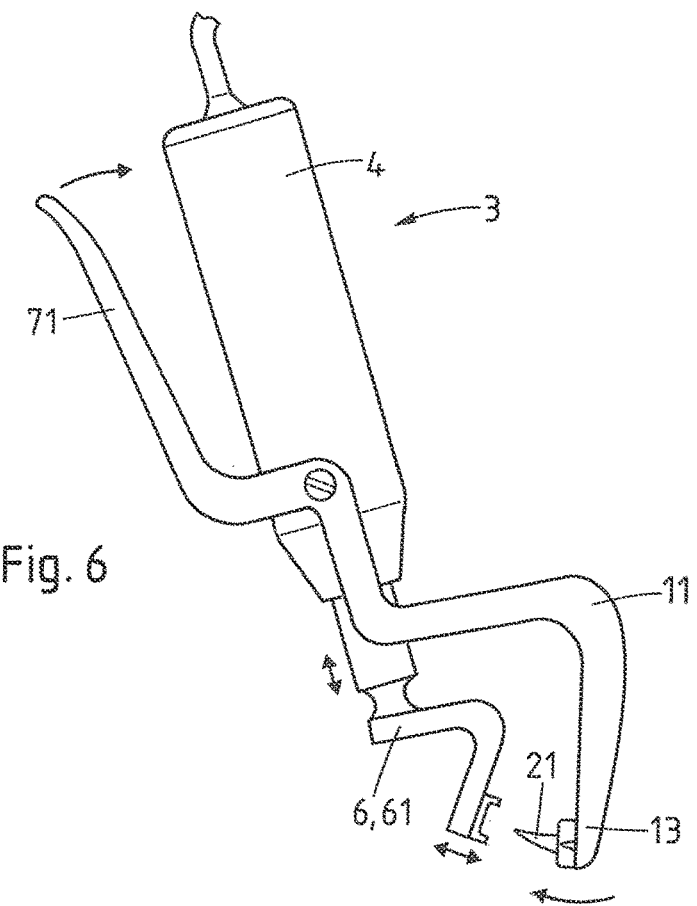
FIG. 6 is an elevation view of a further embodiment of an instrument.

The instrument 3 shown in FIG. 6 is particularly suited for situations where the operation site has to be accessed from a side. The first instrument component 6 has a device 61 that deflects mechanical oscillation from a transversal oscillation along an input axis to a transversal mechanical oscillation along a second axis. Such a device is described in WO 2007/101 362/US 2010/0 179 654 incorporated herein by reference in its entirety. Especially, the embodiment of the oscillation deflection device 61 shown in the figure is based on the device described referring to FIG. 3a and the corresponding description in WO 2007/101 362, however, other embodiments may be used also.

As a further feature, the second instrument component 11 is pivotingly mounted to the housing 4, and the foot 13 may be pressed against the first instrument component 6 by pivoting a lever 71. In the depicted embodiment, the fastener 21 is attached to the second instrument component and is to be inserted from the distal side, however, it would also be possible to provide the fastener at the side of the oscillation deflection device 61.

Figure 7:
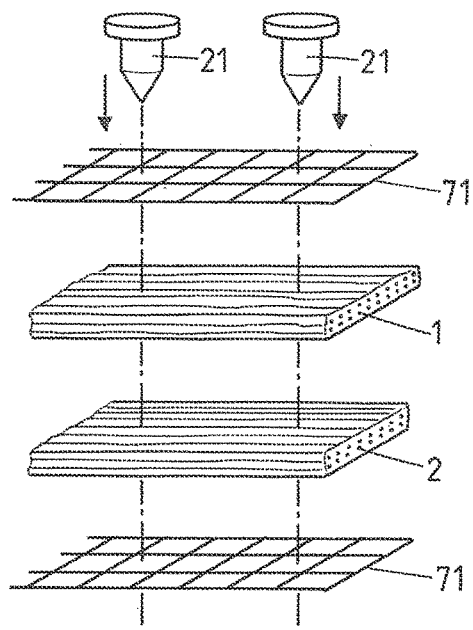
FIG. 7 is a perspective view that illustrates an arrangement that comprises in-plane reinforcement of the tissue parts.

FIG. 7 illustrates the use of a flexibly bendable planar structure of artificial material (or possibly of autograft or allograft tissue), such as a mesh to reinforce the tissue parts and/or their connection. In the configuration shown in FIG. 7, two flexible planar structures being meshes 71 are used, each placed in contact with one of the tissue parts 1, 2. The meshes are placed on the outer sides, so that the tissue parts are in direct contact with each other. The reinforcement provided by the meshes (or other flexible planar structures) may especially be valuable in case multiple fasteners are used, as illustrated by the two fasteners 21 in FIG. 7. The reinforcement can absorb in-plane forces that otherwise would act on the tissue parts at the common opening.

Instead of the depicted configuration with two tissue parts and two outer flexible planar structures, other configurations are possible as described hereinbelow.

Providing only one flexible planar structure, either in contact with one of the tissue parts or between the tissue parts. In the latter case the flexible planar structure may optionally be of a kind promoting the growth of tissue for the tissue parts to adhere to each other.

Providing one or more flexible planar structure(s) instead of one of the tissue parts. The method is then a method of fixing a tissue part to a an implant part, namely to the flexible planar structure that for example reinforces the tissue part or has another function, such as covering and retaining (other) soft tissue, for example in the event of a hernia.

In each of these configurations, using only one fastener or more than two fasteners.

Figure 8A:
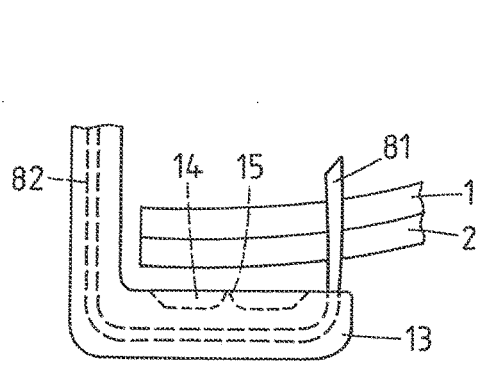
FIGS. 8a and 8b are elevation views showing a way of anchoring a wire or thread.
Figure 8B:
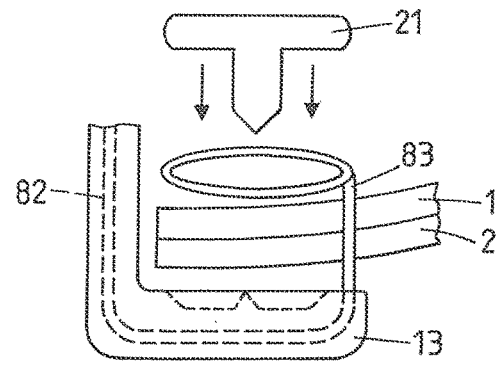

FIGS. 8a and 8b show the use of a guided needle to connect a filament-like element to the tissue part or tissue parts. The foot 13 of a second instrument component comprises a channel through which a bendable needle 81 is guided to pierce the tissue part or tissue parts 1, 2. The needle may for example be of a shape memory material that automatically goes into a stretched configuration after it exits the channel 82 through which it is guided. The needle may for example be of nitinol. The needle is guided by the channel through a part of the foot and then pierces the tissue part or tissue parts from the distal side and exits on the proximal side where it is accessible to the surgeon.

The filament-like element may for example be attached to the needle tip or to an attachment spot close to the needle tip so that the needle pulls it through the tissue part/tissue parts when piercing. Alternatively, the needle may be cannulated, and the filament-like element may be pushed through the cannulation. In these cases, the needle is completely retracted after the filament-like element has been guided through the tissue As yet another alternative, the needle itself or a part of the needle (for example except a nitinol end portion that comprises the sharp tip) may constitute the filament-like element, by being formed into the desired shape after the piercing step.

FIG. 8b shows how the filament-like element's 83 end portion is formed into a loop through which the shaft of the fastener 21 goes. The filament-like element is then attached to the proximal side of the tissue part(s), guided through the piercing hole to the distal side and along the side of the tissue part(s) back to the proximal side. The surgeon may use the filament-like element to thread the tissue part(s)' end portion to some other element or to otherwise excerpt a force on it.

The filament-like element may be a surgical thread or other filament. The loop or other structure attaching the filament-like element to the fastener so that it can be subject to a tensile load may be made prior to the insertion of the fastener 21 or possibly also thereafter. Additionally or as an alternative, the filament-like element may be welded to the fastener during or after insertion of the latter.

Figure 9:
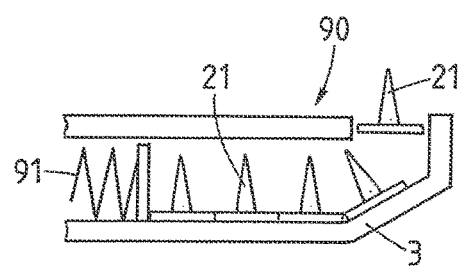
FIG. 9 is an elevation view of a magazine for sequentially dispensing a plurality of fasteners.

FIG. 9 schematically depicts the principle of a foot being provided with a dispenser 90 for automatically dispensing, for example by means of a spring mechanism 91, fasteners, especially for a configuration as described referring to FIGS. 4a-4c.

Figure 10:
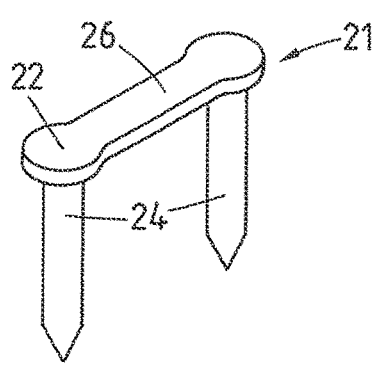
FIG. 10 is a perspective view of a fastener.
Figure 11:
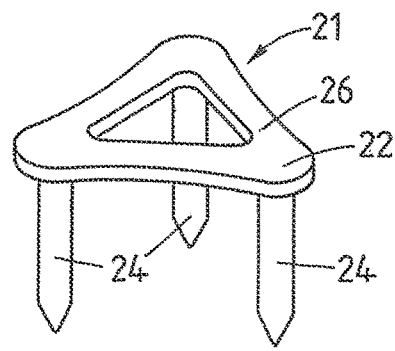
FIG. 11 is a perspective view of a fastener.

Whereas the fasteners 21 in the hereinbefore described embodiments comprise a single fastener body or shaft 24 that is configured to reach through a single common opening of the tissue parts/tissue and implant parts, the invention is also suited for fasteners with a plurality of shafts 24 that are connected by a bridging portion 26 and that are thus configured to reach through a corresponding number of common openings. The bridging portions after the process rest against the tissue (or implant part) and replace or enhance the function of the optional pre-formed (proximal or distal) head 22. FIG. 10 shows an embodiment with two shafts, and FIG. 11 depicts and embodiment with three shafts. Other configurations are possible, for example with more than two shafts in a row, for example, three, four, five, to the point of a comb-like arrangement, or with other geometries that do not form a row like in FIG. 11. Also, any bridge portion shape can be chosen, in accordance with the needs of the surgeon.

Figure 12:
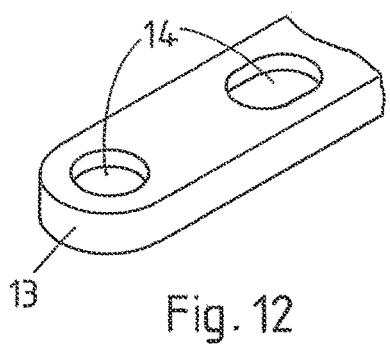
FIG. 12 is a perspective view of a foot.
Figure 13:
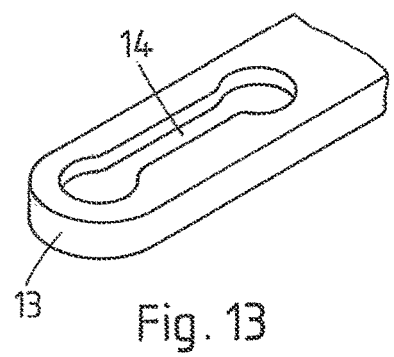
FIG. 13 is a perspective view of a foot.
Figure 14:
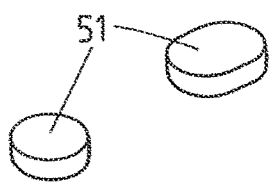
FIG. 14 is a perspective view of a fastener head forming element.
Figure 15:
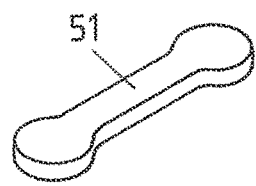
FIG. 15 is a perspective view of a fastener head forming element.

The instrument component in contact with which the head is formed (generally, the instrument component with the head shaping portion and/or with the head forming element(s) is configured correspondingly. For embodiments where the fastener 21 is inserted from the proximal side, this concerns the foot 13 of the second instrument component. FIGS. 12-15 illustrate this for the example fastener of FIG. 10. In FIG. 12, the foot comprises two head shaping indentations for shaping a head at the distal end of each of the two shaft portions so that the fastener after being implanted comprises two distal heads. An alternative is depicted in FIG. 13. A common head shaping indentation forms a distal head that also comprises a bridge portion, like the pre-shaped proximal portion of the fastener. The same principles apply in case the distal head is provided using a head forming element. As a first option, two individual head forming elements 51 are provided (FIG. 14), whereas a second option suggests a common head forming element 51 that has a bride portion.

Whereas FIGS. 12-15 relate to configurations where the fastener is inserted from the proximal side and comprises two shafts, same considerations apply for fasteners inserted from the distal side and/or with more than two shafts.

What is claimed is:

1. A method of fixing a first and a second part to each other, the method comprising the steps of
providing a fastener comprising a thermoplastic material,
providing a fastening instrument, the fastening instrument comprising a first instrument component with a first contact surface and a second instrument component with a second contact surface, the first instrument component and the second instrument component being displaceable with respect to each other,
positioning the fastener and the fastening instrument so that the fastener reaches through a common opening of the first and second parts, which common opening is constituted by a first through opening of the first part and a second through opening of the second part, the first and second through openings aligned with each other, and so that the first contact surface is in contact with a proximal end face of the fastener and the second contact surface is in contact with a distal end face of the fastener, submitting the first and second instrument components to a relative force so that the fastener is pressed between the first and second contact surfaces, and simultaneously coupling mechanical vibrations into at least one of the first and second instrument components with a vibration power and during a vibration time sufficient to at least partially soften and/or melt an end portion of the fastener under the common impact of the relative force and the vibrations, and using the softening and/or melting of the end portion to provide the end portion with a head with a diameter greater than a diameter of at least one of the through openings, and letting the softened and/or melted end portion re-solidify; wherein the method comprises the further step of providing a filament-like element and causing the filament-like element to form a loop portion, wherein after the step of letting the softened and/or melted end portion re-solidify the loop portion encircles a portion of the fastener, wherein either the first part is a first tissue part and the second part is a second tissue part or wherein the first part is a tissue part and the second part is an implant part.

2. The method according to claim 1, wherein in the step of using the softening and/or melting of the end portion to provide the end portion with a head, the end portion is caused to deform, under the common impact of the relative force and the vibrations, to yield the head.

3. The method according to claim 2, wherein the end portion itself is deformed into the head.

4. The method according to claim 1, wherein prior to the step of submitting the first and second instrument components to a relative force and coupling mechanical vibrations into at least one of the instrument components, a head forming element is provided, and wherein during said step of submitting the first and second instrument components to a relative force and coupling mechanical vibrations into at least one of the instrument components, the head forming element is in contact with the end portion and is, by the softening and/or melting, welded to the end portion so that the head is formed.

5. The method according to claim 1, wherein the fastener is positioned by being inserted from a proximal side, wherein the end portion that is provided with a head is a distal portion, and wherein the head is a distal head.

6. The method according to claim 1, wherein prior to the step of positioning the fastener, the fastener is temporarily mounted to the second instrument component, and wherein the fastener is positioned by being inserted from a distal side.

7. The method according to claim 1, comprising the further step of placing, prior to the step of positioning the fastener, a flexible planar structure of an artificial material in contact with at least one of the first part or the second part, wherein in the step of positioning the fastener, the fastener is positioned to reach through an opening of the flexible planar structure.

8. The method according to claim 1, wherein after the step of letting the softened and/or melted end portion re-solidify the loop portion is covered by the head.

* * * * *